United States Patent [19]

Glasebrook

[11] Patent Number: 5,708,009
[45] Date of Patent: Jan. 13, 1998

[54] METHODS OF INHIBITING MYELOPEROXIDASE ACTIVITY

[75] Inventor: Andrew L. Glasebrook, Zionsville, Ind.

[73] Assignee: Eli Lilly and Company, Indianapolis, Ind.

[21] Appl. No.: 171,330

[22] Filed: Dec. 21, 1993

[51] Int. Cl.$^6$ .................. A61K 31/445; A61K 31/40; A61K 31/385
[52] U.S. Cl. ................. 514/324; 514/428; 514/443
[58] Field of Search .................. 514/320, 324, 514/428, 443

[56] References Cited

U.S. PATENT DOCUMENTS

| | | |
|---|---|---|
| 4,133,814 | 1/1979 | Jones et al. . |
| 4,380,635 | 4/1983 | Peters . |
| 4,418,068 | 11/1983 | Jones . |
| 5,075,321 | 12/1991 | Schreiber . |

FOREIGN PATENT DOCUMENTS

| | | |
|---|---|---|
| WO93/10113 | 5/1993 | WIPO . |
| WO93/1074 | 6/1993 | WIPO . |

OTHER PUBLICATIONS

Keeping et al., Endocrinology, 111 (6), 2046–2054 (1982).
U.S. application No. 08/081,610, Yang, filed Jun. 21, 1993.
Draper et al., "Effects of Raloxifene (LY139481 HCL) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.
Bryant et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti–estrogen Raloxifene", Am Soc. Bone & Min. Res., Tampa, Sep. 18–22, 1993.
Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.
Sato et al., "DEXA Analysis of Raloxifene Effects on the Bones From Ovariectomized Rats", Am. Soc. for Bone and Min. Res., Tampa, Sep. 18–22, 1993.
Yang et al., "Raloxifene an Anti–Estrogen, Simulates the Effects of Estrogen in Inhibiting Bone Resorption Through Regulating TGFB-3 Expression in Bone;".Am Soc. for Bone and Min. Res., Tampa, Sep. 18–22, 1993.
Black et al., "Distinct, Structure–Related Profiles of Estrogenic and Anti–Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.
Black et al., "Differential Interaction of Antiestrogens with Cytosol Estrogen Receptors," Molecular and Cellular Endocrinology, 22:1981, 95–103.
Black et al., "Evidence for Biological Action of the Antiestrogens LY117018 and Tamoxifen by Different Mechanisms," Endocrinology 109;1981, 987–989.
Black, L.J. "Biological Actions and Binding Properites of a New Estrogen Antagosist LY117018,"In: Homone Antagonists, 129–82, 1982 (M.K. Agarwal ed.) Walter de Gruyter and Co., Berlin New York.
Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.
Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.
Black et al., Antagonism of Estrogen Action with a New benzothiophene Derived Antiestrogen, Life Sciences, 32:1983. 1031–1036.

(List continued on next page.)

Primary Examiner—Zohreh Fay
Attorney, Agent, or Firm—James J. Sales

[57] ABSTRACT

A method of inhibiting myeloperoxidase activity or a physiological condition associated with an excess thereof, comprising administering to a human in need thereof an effective amount of a compound having the formula

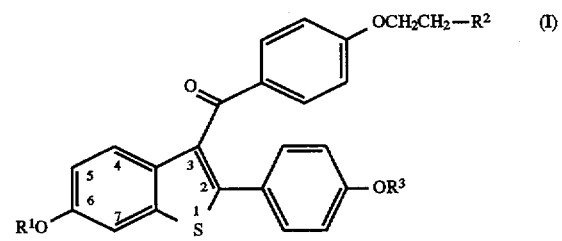

wherein
R$^1$ and R$^3$ are independently hydrogen, —CH$_3$,

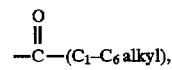

or

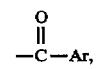

wherein Ar is optionally substituted phenyl;
R$^2$ is selected from the group consisting of pyrrolidine, hexamethyleneamino, and piperidino; or a pharmaceutically acceptable salt of solvate thereof.

9 Claims, No Drawings

OTHER PUBLICATIONS

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl) ethoxyl]–phenyl]methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

Jansson, *Free Rad. Res. Comm.*, 14(3), 195–208, 1991.

METHODS OF INHIBITING MYELOPEROXIDASE ACTIVITY

BACKGROUND OF THE INVENTION

Autoimmune diseases involve aberrant regulation of cellular and humoral mediated immunity and are frequently associated with abnormal or enhanced T cell, B cell and macrophage effector functions directed towards self antigens. The activation of these cellular components towards self antigens is believed related to the break in feedback mechanisms associated with self tolerance. Autoimmune diseases encompass a whole spectrum of clinical entities and despite the differences in the target organ have many similarities. These include their preponderance in females of child bearing age with a female to male ratio varying from 50:1 in Hashimoto's throiditis to 10:1 in Systemic lupus erythematosus to 2:1 in Myasthenia gravis (Ahmed et al., Am J. Path., 121:531 (1985)). In addition, these diseases are all characterized by their chronicity, the tendency of clinical remission and "flare ups" for poorly understood reasons, and the involvement of other organs. While the presence of autoantibodies, inappropriate expression of class II antigens, macrophage activation and T cell infiltration to the target organ have been described in essentially all of the autoimmune diseases, neither the triggering mechanisms which result in disease activation nor disease progression are well understood. Accordingly, therapy for these diseases is largely unsatisfactory and involves the use of gold salts, methotrexate, antimalarials, glucocorticoids (methylprednisolone), and other immunosuppressives as well as plasmaphoresis and attempts at inducing tolerance. Treatment of autoimmune diseases has not improved significantly over the past decade and primarily is associated with the use of nonsteroidal and steroidal anti-inflammatory agents to treat the symptoms of the disease. Clearly while suppression of the specific immune response directed against the host is necessary, generalized immunosuppression as with glucocorticoids has major liabilities in terms of side effect profile and the propensity of the immunosuppressed patient to be at greater risk for other infectious and non-infectious diseases.

Polymorphonuclear leukocytes (PMNL) play a regulatory role in inflammatory diseases. These cells, when activated, synthesize and release oxygen-centered molecules, chemoattractents, and hydrolyric enzymes. There is evidence that the oxygen-centered molecules play a detrimental role in a number of diseases such as chronic inflammatory diseases, rheumatoid arthritis, SLE, and others. In the case of an autoimmune disease, SLE, for example, the initiation of an inflammatory response are self antigen stimulating one's host neutrophils or PMNLs to secrete strong oxidants which damage surrounding cells and tissue.

Estrogen appears to be involved with autoimmune diseases although its role in disease progression or regression is complex and dependent on the nature of the autoimmune disease. Estrogen for example appears to have an ameliorating effect on rheumatoid arthritis while having an exacerbating effect on systemic lupus (Chander & Spector; Ann. Rheum. Dis. 50:139). As reported by Jansson (Free Rad Res Comms, 14(3), 195–208, (1991), incorporated herein by reference), estrogen increased the activity of an enzyme generated by PMNLs, myeloperoxidase, which regulates the production of oxidants from hydrogen peroxide. This enzyme converts hydrogen peroxide to hypochlorous acid, a strong oxidant. By increasing the enzyme's activity, and thus the presence of hypochlorous acid, the liklihood of increased oxidative stress on tissues, cells and various macromolecules in chronic inflammatory/autoimmune diseases is enhanced.

SUMMARY OF THE INVENTION

This invention provides methods for inhibiting myeloperoxidase activity comprising administering to a human in need thereof an effective amount of a compound of formula I

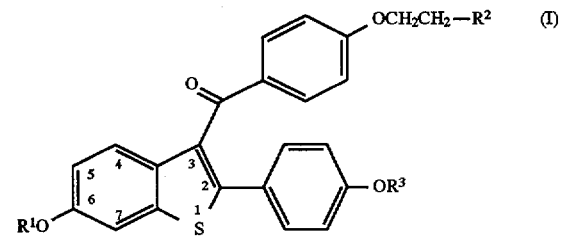

wherein
R$^1$ and R$^3$ are independently hydrogen, —CH$_3$,

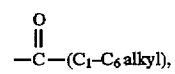

or

wherein Ar is optionally substituted phenyl;
R$^2$ is selected from the group consisting of pyrrolidino, hexamethyleneimino, and piperidino; and pharmaceutically acceptable salts and solvates thereof.

The invention also encompasses a method for inhibiting a physiological condition associated with excess myeloperoxidase, comprising administering to a human in need thereof an effective amount of a compound of formula 1.

DETAILED DESCRIPTION OF THE INVENTION

The current invention concerns the discovery that a select group of 2-phenyl-3-aroylbenzothiophenes (benzothiophenes), those of formula I, are useful for inhibiting myeloperoxidase activity or a physiological condition due, at least in part, to an excess of the enzyme activity or protein thereof. The therapeutic and prophylactic treatments provided by this invention are practiced by administering to a human in need thereof a dose of a compound of formula I or a pharmaceutically acceptable salt or solvate thereof, that is effective to inhibit myeloperoxidase activity or physiological conditions caused at least in part thereby.

The term "inhibit" includes its generally accepted meaning which includes prohibiting, preventing, restraining, and slowing, stopping or reversing progression, severity or a resultant symptom. As such, the present method includes both medical therapeutic and/or prophylactic administration, as appropriate.

The term "physiological condition associated with an excess of myeloperoxidase" encompasses those disorders associated with an inappropriate amount or reaction to myeloperoxidase present, or the effect or activity of such, in a locale. Examples of such conditions, includes systemic lupus erythrematosas, Hashimoto's thyroiditis, myasthenia gravis, rheumatoid arthritis, multiple sclerosis, Guillan Barre syndrome, and glomerulonephritis.

Raloxifene is a preferred compound of this invention and it is the hydrochloride salt of a compound of formula 1 wherein $R^1$ and $R^3$ are hydrogen and $R^2$ is 1-piperidinyl.

Generally, at least one compound of formula I is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. The term "optionally substituted phenyl" includes phenyl and phenyl substituted once or twice with $C_1$-$C_6$ alkyl, $C_1$-$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit myeloperoxidase activity or a physiological condition associated therewith, according to this invention, will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed to effectively treat or prevent activity or condition.

It is usually preferred to administer a compound of formula I in the form of an acid addition salt, as is customary in the administration of pharmaceuticals bearing a basic group, such as the piperidino ring. It is preferred to administer a compound of the invention to an aging human (e.g. a post-menopausal female). For such purposes the following oral dosage forms are available.

FORMULATIONS

In the formulations which follow, "Active ingredient" means a compound of formula I.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2: Raloxifene Capsule

| Ingredient | Quantity (mg/capsule) |
| --- | --- |
| Raloxifene | 1 |
| Starch, NF | 112 |
| Starch flowable powder | 225.3 |
| Silicone fluid 350 centistokes | 1.7 |

Formulation 3: Raloxifene Capsule

| Ingredient | Quantity (mg/capsule) |
| --- | --- |
| Raloxifene | 5 |
| Starch, NF | 108 |
| Starch flowable powder | 225.3 |
| Silicone fluid 350 centistokes | 1.7 |

Formulation 4: Raloxifene Capsule

| Ingredient | Quantity (mg/capsule) |
| --- | --- |
| Raloxifene | 10 |
| Starch, NF | 103 |
| Starch flowable powder | 225.3 |
| Silicone fluid 350 centistokes | 1.7 |

Formulation 5: Raloxifene Capsule

| Ingredient | Quantity (mg/capsule) |
| --- | --- |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of Active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of Active ingredient per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

ASSAYS

Assay 1

In order to investigate the myeloperoxidase activity inhibiting properties of compounds of formula 1, Assays 1 and 2, as set out in Jansson (supra.), are employed.

In this assay, human PMN leukocytes are stimulated with estriol to increase myeloperoxidase activity in the presence of added hydrogen peroxide. The conversion of luminol by hypochlorous acid is measured by chemiluminescence. The reaction mix consists of cells ($10^6$), agent or compound of formula 1 (1 µM), hydrogen peroxide (0.1 mM), and luminol (0.2 mM) incubated at 37° C.

| Agent | Light Units |
|---|---|
| None | 1.57 |
| Tamoxifen | 2.00 |
| ICI 164,334 | 1.74 |
| 17-β-estradiol | 3.426 |
| Raloxifene | 1.967 |
| Estrione | 2.425 |
| Estriol | 2.76 |
| Estriol + Tamoxifen | 2.69 |
| Estriol + ICI | 2.40 |
| Estriol + Raloxifene | 1.26 |

Estrogen and its analogs stimulate myeloperoxidase activity as measured above. Raloxifene, but not tamoxifen, antagonizes the estriol stimulated chemiluminescence.

Assay 2

Purified human myeloperoxidase is incubated with agent (estrogen or compound A), in the presence of luminol at 37° C. The substrate, hydrogen peroxide, is added and the chemiluminescence measured. The reaction mix is human MPE (250 ng), agent or Compound A (10 µM, titrated), hydrogen peroxide (1 mm), and luminol (0.2 mm). In the following, Compound A is a compound where $R^1$ and $R^3$ are hydrogen, and $R^2$ is 1-pyrrolidino.

| CONDITION | LIGHT UNITS |
|---|---|
| No MPE | |
| Estrone | 1.43 |
| Estriol | 1.44 |
| Compound A | 1.30 |
| With MPE | |
| DMSO | 10.67 |
| Estrone | 9.60 |
| DMSO | 11.36 |
| Estriol | 11.55 |
| DMSO | 10.48 |
| Compound A | 6.43 |

Estrogen and its analog have little or no effect on MPE activity, however, Compound A reduced by about 50% the activity of purified MPE.

Assay 3

Five to fifty women are selected for the clinical study. The women suffer from SLE or rheumatoid arthritis. Because of the idiosyncratic and subjective nature of these disorders, the study has a placebo control group, i.e., the women are divided into two groups, one of which receives a compound of formula 1 as the active agent and the other receives a placebo. Women in the test group receive between 50–200 mg of the drug per day by the oral route. They continue this therapy for 3–12 months. Accurate records are kept as to the number and severity of the symptoms in both groups and at the end of the study these results are compared. The results are compared both between members of each group and also the results for each patient are compared to the symptoms reported by each patient before the study began.

Utility of the compounds of formula I is illustrated by the positive impact they have in at least one of the assays described above.

We claim:

1. A method of inhibiting myeloperoxidase activity comprising administering to a human in need thereof an effective amount of a compound having the formula

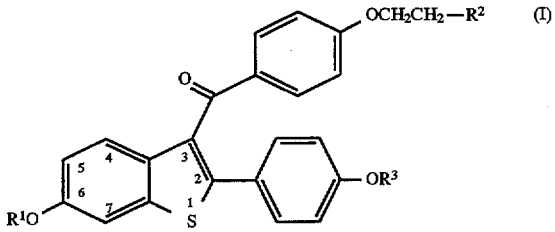

wherein $R^1$ and $R^3$ are independently hydrogen, —$CH_3$,

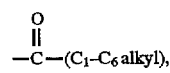

or

wherein Ar is optionally substituted phenyl;

$R^2$ is selected from the group consisting of pyrrolidine, hexamethylenemino, and piperidino; or a pharmaceutically acceptable salt of solvate thereof.

2. The method of claim 1 wherein said compound is the hydrochloride salt thereof.

3. The method of claim 1 wherein said compound is

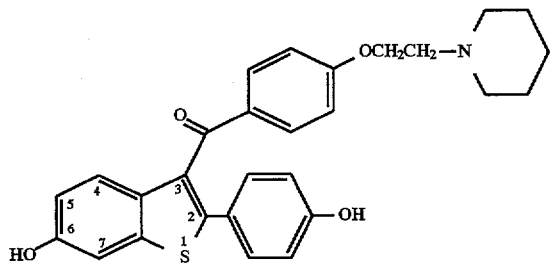

or its hydrochloride salt.

4. The method of claim 1 wherein said human is a post-menopausal woman.

5. A method for the inhibition of a physiological disorder associated with an excess of myeloperoxidase, which method comprises administering to a human in need thereof an effective amount of a compound of Formula I

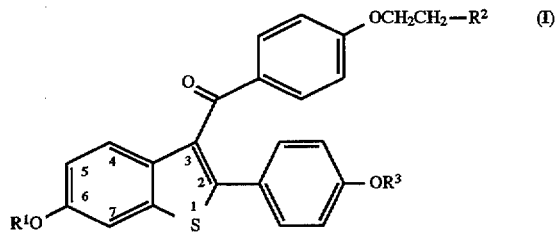

wherein $R^1$ and $R^3$ are independently hydrogen, —$CH_3$,

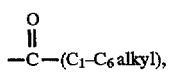

or

wherein Ar is optionally substituted phenyl;

$R^2$ is selected from the group consisting of pyrrolidine, hexamtehylenemino, and piperidino; or a pharmaceutically acceptable salt of solvate thereof.

6. The method of claim 5 wherein said compound is the hydrochloride salt thereof.

7. The method of claim 5 wherein said administration is prophylactic.

8. The method of claim 5 wherein said compound is

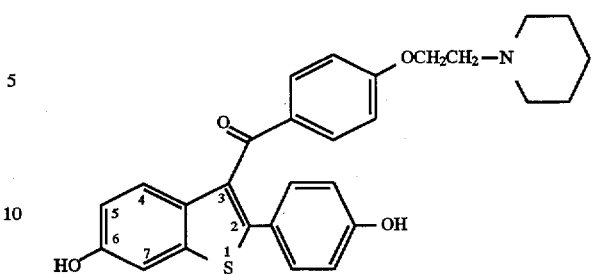

or its hydrochloride salt.

9. The method of claim 5 wherein said disorder is selected from systemic lupus erythrematosas, Hashimoto's thyroiditis, myasthenia gravis, rheumatoid arthritis, multiple sclerosis, Guillan Barre syndrome, or glomerulonephritis.

* * * * *